(12) United States Patent
Tuszynski et al.

(10) Patent No.: US 7,217,428 B2
(45) Date of Patent: May 15, 2007

(54) DRUG DELIVERY APPARATUS UTILIZING CANTILEVER

(75) Inventors: Jack Tuszynski, Edmonton (CA); Nancy J. Woolf, Studio City, CA (US)

(73) Assignee: Technology Innovations LLC, West Henrietta, NY (US)

( * ) Notice: Subject to any disclaimer, the term of this patent is extended or adjusted under 35 U.S.C. 154(b) by 313 days.

(21) Appl. No.: 10/857,279

(22) Filed: May 28, 2004

(65) Prior Publication Data
US 2005/0265991 A1    Dec. 1, 2005

(51) Int. Cl.
*A61K 9/20* (2006.01)
*A61K 9/22* (2006.01)
*H01L 21/00* (2006.01)

(52) U.S. Cl. .................. 424/464; 604/891.1; 438/52

(58) Field of Classification Search ............ 424/130.1, 424/408, 422, 423, 427, 451, 464, 468; 514/449; 604/31, 502, 503, 504, 66, 67, 890.1, 891.1; 438/49, 52, 53
See application file for complete search history.

(56) References Cited

U.S. PATENT DOCUMENTS

| | | | |
|---|---|---|---|
| 4,642,291 A | 2/1987 | Cairncross | |
| 5,029,805 A | 7/1991 | Albarda | |
| 5,134,075 A | 7/1992 | Hellstrom | |
| 5,161,774 A | 11/1992 | Engelsdorf | |
| 5,176,358 A | 1/1993 | Bonne | |
| 5,180,623 A | 1/1993 | Ohnstein | |
| 5,197,517 A | 3/1993 | Perera | |
| 5,238,223 A | 8/1993 | Mettner | |
| 5,242,824 A | 9/1993 | Hellstrom | |
| 5,254,209 A | 10/1993 | Schmidt | |
| 5,309,943 A | 5/1994 | Stevenson | |
| 5,322,258 A | 6/1994 | Bosch | |
| 5,333,831 A | 8/1994 | Barth | |
| 5,364,742 A | 11/1994 | Fan | |
| 5,417,235 A | 5/1995 | Wise | |
| 5,445,008 A | 8/1995 | Wachter | |
| 5,475,318 A | 12/1995 | Marcus | |
| 5,559,202 A | 9/1996 | Yoshikawa | |
| 5,581,083 A | 12/1996 | Majumdar | |
| 5,584,807 A | 12/1996 | McCabe | |
| 5,595,904 A | 1/1997 | Boulton | |
| 5,643,247 A | 7/1997 | Fernandez | |
| 5,649,423 A | 7/1997 | Sniegowski | |
| 5,676,850 A | 10/1997 | Reed | |
| 5,719,324 A | 2/1998 | Thundat | |
| 5,760,092 A | 6/1998 | Timasheff | |
| 5,770,076 A | 6/1998 | Chu | |

(Continued)

OTHER PUBLICATIONS

Low, L.M., et al., "Microactuators toward microvalves for responsive controlled drug delivery" Sensors and Actuators, B 67 (2000) 149-160.*

(Continued)

*Primary Examiner*—Sharon E. Kennedy
(74) *Attorney, Agent, or Firm*—Buchanan Ingersoll & Rooney PC

(57) ABSTRACT

Disclosed is a device which employs a chemically sensitive cantilever hingably attached to a capsule. The cantilever functions as a switch which regulates the flow of particles into and/or out of the capsule.

15 Claims, 11 Drawing Sheets

U.S. PATENT DOCUMENTS

| | | | |
|---|---|---|---|
| 5,770,722 | A | 6/1998 | Lockhart |
| 5,776,751 | A | 7/1998 | Boulton |
| 5,807,758 | A | 9/1998 | Lee |
| 5,858,653 | A | 1/1999 | Duran |
| 5,865,796 | A | 2/1999 | McCabe |
| 5,872,006 | A | 2/1999 | Boulton |
| 5,908,981 | A | 6/1999 | Atalar |
| 5,914,261 | A | 6/1999 | Boulton |
| 5,918,263 | A | 6/1999 | Thundat |
| 5,919,548 | A | 7/1999 | Barron |
| 5,956,575 | A | 9/1999 | Bertin |
| 5,976,390 | A | 11/1999 | Muramatsu |
| 5,980,896 | A | 11/1999 | Hellstrom |
| 5,994,084 | A | 11/1999 | Anderton |
| 5,998,995 | A | 12/1999 | Osiander |
| 6,016,686 | A | 1/2000 | Thundat |
| 6,025,337 | A | 2/2000 | Truong |
| 6,096,559 | A | 8/2000 | Thundat |
| 6,120,767 | A | 9/2000 | Robinson |
| 6,136,243 | A | 10/2000 | Mehregany |
| 6,156,216 | A | 12/2000 | Manalis |
| 6,212,939 | B1 | 4/2001 | Thundat |
| 6,247,720 | B1 | 6/2001 | Linger |
| 6,248,720 | B1 | 6/2001 | Mathiowitz |
| 6,254,890 | B1 | 7/2001 | Hirosue |
| 6,262,034 | B1 | 7/2001 | Mathiowitz |
| 6,277,963 | B1 | 8/2001 | Boulton |
| 6,289,717 | B1 | 9/2001 | Thundat |
| 6,297,035 | B1 | 10/2001 | Boulton |
| 6,303,358 | B1 | 10/2001 | Boulton |
| 6,311,549 | B1 | 11/2001 | Thundat |
| 6,326,489 | B1 | 12/2001 | Church |
| 6,368,275 | B1* | 4/2002 | Sliwa et al. ............... 600/437 |
| 6,393,685 | B1 | 5/2002 | Collins |
| 6,410,517 | B1 | 6/2002 | Truong |
| 6,420,176 | B1 | 7/2002 | Lisziewicz |
| 6,436,708 | B1 | 8/2002 | Leone |
| 6,472,739 | B1 | 10/2002 | Wood |
| 6,475,779 | B2 | 11/2002 | Mathiowitz |
| 6,491,666 | B1* | 12/2002 | Santini et al. ............. 604/191 |
| 6,498,257 | B1 | 12/2002 | Vite |
| 6,523,392 | B2 | 2/2003 | Porter |
| 6,524,890 | B2 | 2/2003 | Ueda |
| 6,525,307 | B1 | 2/2003 | Evans |
| 6,528,167 | B2 | 3/2003 | O'Gara |
| 6,548,021 | B1 | 4/2003 | Church |
| 6,551,849 | B1 | 4/2003 | Kenney |
| 6,576,489 | B2 | 6/2003 | Leung |
| 6,589,198 | B1 | 7/2003 | Soltanpour |
| 6,620,617 | B2 | 9/2003 | Mathiowitz |
| 6,660,533 | B2 | 12/2003 | Mallet |
| 6,677,313 | B1 | 1/2004 | Mathiowitz |
| 6,706,203 | B2 | 3/2004 | Barth |
| 6,712,480 | B1 | 3/2004 | Leung |
| 6,713,272 | B2 | 3/2004 | Anderson |
| 6,730,269 | B2 | 5/2004 | Mirkin |
| 6,730,487 | B2 | 5/2004 | Latov |
| 6,738,141 | B1 | 5/2004 | Thirstrup |
| 2002/0123048 | A1 | 9/2002 | Gau |
| 2003/0008335 | A1 | 1/2003 | Marx |
| 2003/0010097 | A1 | 1/2003 | Porter |
| 2003/0023187 | A1 | 1/2003 | Tapper |
| 2003/0026754 | A1 | 2/2003 | Clarke |
| 2003/0032892 | A1 | 2/2003 | Erlach |
| 2003/0040682 | A1 | 2/2003 | Tapper |
| 2003/0045019 | A1 | 3/2003 | Kubena |
| 2003/0069560 | A1* | 4/2003 | Adamis et al. ............. 604/521 |
| 2005/0177223 | A1* | 8/2005 | Palmaz ....................... 623/1.15 |
| 2005/0186241 | A1* | 8/2005 | Boyle et al. ................ 424/423 |
| 2006/0074479 | A1* | 4/2006 | Bailey et al. .............. 623/1.13 |

OTHER PUBLICATIONS

U.S. Appl. No. 60/503,988, filed Sep. 18, 2003 by Palmaz.*
Kirsch, R. et al., Three-dimensional metallization of microtubules, Thin Solid Films, v305, pp. 248-253, 1997.
Zaric, Sasa, et al., Optical Signatures of the Aharonov-Bohm Phase in Single-Walled Carbon Nanotubes, Science, v304, pp. 1129-1134, May 21, 2004.
Baker, N.A. et al., Electrostatics of nanosystems: application to microtubules and the ribosome, Proc of the Nat. Acad. of Sciences, v98, n18, pp. 10037-10041, Aug. 28, 2001.
D'Andrea, MichaelR. et al, Abnormal patterns of microtubule-associated protein-2 (Map-2) immunolabeling in neuronal nuclei and Lewy bodies in Parkinson's disease substantia nigra brain tissues, Neuroscience Letters, v306, pp. 137-140 2001.
Abadal, G. et al., Electromechanical model of a resonating non-cantilever-based sensor for high-resolution and high-sensitivity mass detection, Nanotechnology, v12, pp. 100-104, 2001.
Hess, Henry, Light-Controlled Molecular Shuttles made from Motor Proteins Carrying Cargo on Engineered Surfaces, Nano Letters, v1, No. 5, pp. 235-239, 2001.
Zhou, Jun, et al., Brminated Derivatives of Noscapine are potent microtubule-interfering agents that perturb mitosis andinhibit cell proliferation, Molecular Pharmacology, v63, n4, pp. 799-807, 2003.
Muthukumar, M., Polymer escape through a nanopore, J. of Chemical Physics, v118, n11, pp. 5174-5184, 2003.
Schuessler, Hans A. et al., Surface plasmon resonance study of the actin-myosin sarcomeric complex and tublin dimers, J. of Modern Optics, v50, No. 15-17, pp. 2381-2391, 2003.
Liu, Yu, et al., Influences of preparation conditions on particle size and DNA-loading efficiency for poly(DL-lactic acid-polyethylene glycol) microspheres entrapping free DNA, J. of Controlled Release, v83, pp. 147-155, 2002.
Hoffner, G., et al., Perinuclear localization of huntingtin as a consequence of its binding to microtubules through an interaction of beta-tubulin: relevance to Huntington's disease, J. of Cell Science, v115, n5, pp. 941-948, 2002.
Wang, J. et al., Enhanced gene expression in mouse muscles by sustained release of plasmid DNA using PPE-EA as a carrier, Gene Therapy, v9, pp. 1254-1261, 2002.
Datskos, P.G., et al., Micro and Nanocantilever Sensors, Encyclopedia of Nanoscience and Nanotechnology, vol. X, pp. 1-10.
Loring J.F., Correction of article in DNA and Cell Biology, DNA and Cell Biology, v21, n3, pp. 241-244, 2002.
Loring J.F., A gene Expression Profile of Alxheimer'Disease, DNA and Cell Biology, v20, n11, pp.683-695, 2001.
Kustanovich, T., Metastable Network Model of Protein Transport through Nuclear Pores, Biophysical Journal, v86, n4, pp. 2008-2016, 2004.
Hiratsuka, Yuichi, et al., Controlling the Direction of Kinesin-Driven Microtubule Movements along Microlithographic Tracks, Biophysical Journal, v81, pp. 1555-1561, 2001.
Fattal, Elias, Liposome-entrapped Ampicillin in the Treatment of Experimental Murine Listeriosis and Salmonellosis, Antimicrobial Agents and Chemotherapy, v35, n4, 1991.
Hu, Yuan Yuan, et al., Levels of Nonphosphorylated and phosphorylated tau in cerebrospinal fluid of Alzheimer's disease patients, Am. J. of Pathology, v160, n4, pp. 1269-1278, 2002.
Lambert, G., et al., Nanoparticulate systems for the delivery of antisense oligonucleotides, Advanced Drug Delivery Reviews, v47, pp. 99-112, 2001.
Sayre, Lawrence M., et al., In Situ Oxidative Catalysis by Neurofibrillary Tangles and Senile Plaques in Alzheimer's Disease: A Central Role for Bound Transition Metals, J. of Neurochemistry, v74, n1, pp. 270-279, 2000.
Haramus, V, Surfactant and polymer-surfactant aggregates in solution, Institute of Materials Research [online], [Retrieved on May 24, 2004] <URL: www.gkss.de/pages.php?page=w_abl_wfs_general. html&language=d&version=g>.

Kindler, Stefan, et al., Molecular Structure of Microtubule-associated Protein 2b and 2c from Rat Brain, The Journal of Biological Chemistry, v265, n32, pp. 19679-19684, 1990.

Haw, Mark, Arrows point to nanotech's future, Nature, [online], [Retrieved on May 24, 2004] <URL: www.nature.com/nsu/010920/010920-8.html> Sep. 19, 2001.

Weiss, Ingrid K. et al., Imaging Microtubules, Kinesin Decorated Microtubules and Kinesin Using Tapping Mode Atomic Force Microscopy in Fluids, [online], [retrieved on May 24, 2004]. <URL:http://www.biophysik.uni-brernen.de/radmacher/publications/microtubule.html>.

UNKNOWN, Magnetic forces may turn some nanotubes into metals, Innovations Report, [online], [retrieved on May 24, 2004], <URL: www.innovations-report.de/html/berichte/materialwissenschalten/bericht-29457.html>.

Paul, M.R.; Radovitzky, R.; Cross; M.C.; The design of a biodetector. 55th Annual Meeting of the Divison of Fluid Dynamics, APS, Dallas, TX, Nov. 24-26, 2002.

Chi, Pei-Ying, Nano Cantilever Type for Biological Sensing (DNA), slides from oral presentation of Dec. 17, 2003.

Coskun U.C., et al., h/e Magnetic Flux Modulation of the Energy Gap in Nanotube Quantum Dots, Science v304, pp. 1132-1134, May 21, 2004.

Mershin A., et al., Tubulin dipole moment, dielectric constant and quantum behavior: computer siluations, experimental results and suggestions. [online] [retrieved on May 24, 2004] <URL: http://arxiv.org/abs/physics/0402053>.

Yamaguchi, H. et al., Fabrication and characterization of novel semiconductor nanomechanical structures. Surf. Sci. 532, 1171 (2003).

Unknown, Map-2 protein sequence listing for rats and humans, [online] [retrieved on May 19, 2004] <URL: http://www.ncbi.nlm.nih.gov/entrez/query.fcgi?CMD=Search&DB=protein>.

Lee, S.B. and Martin C.R.; Electromodulated Molecular Transport in Gold-Nanotube Membranes, J. Am. Chem. Soc. v124 pp. 11850-11851 (2002).

Maaloum M., et al., Approaching microtubule structure with the scanning tunneling microscope (STM), J. Cell Sci. v107 pp. 3127-3131 (1994).

International Search Report issued in corresponding PCT/US05/13487 on Aug. 23, 2006.

* cited by examiner

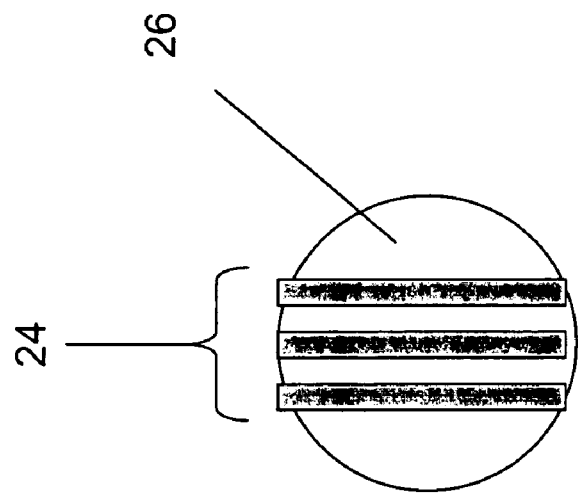
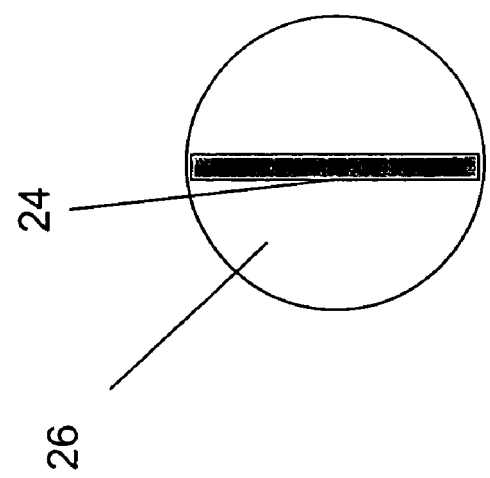
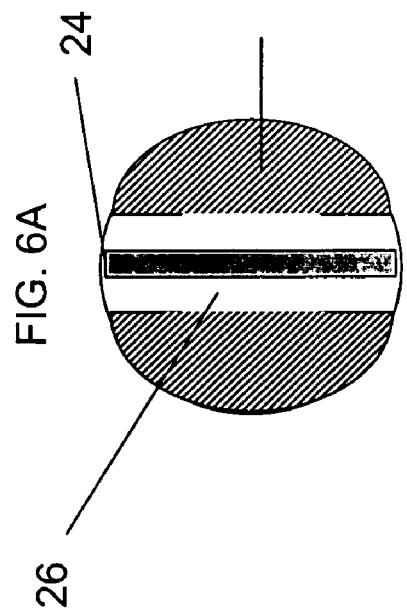
FIG. 6A
FIG. 6B
FIG. 6C
FIG. 6

DRUG DELIVERY APPARATUS UTILIZING CANTILEVER

FIELD OF THE INVENTION

This invention relates, in one embodiment, to the controlled release of compounds through the use of a chemically sensitive cantilever.

BACKGROUND OF THE INVENTION

The prior art is replete with attempts to deliver therapeutic agents to a specific cell. Chemotherapeutic agents, for example, preferentially exert their effects at tumor cites due to the prolific cell growth that occurs in cancerous tissues. It has been a long standing objective to control the delivery of biologically active compounds and/or exogenous genes ("gene therapy") to a cell.

Virus-like particles, often derived from known viruses, have been adapted to carry therapeutic agents. Using such methodology a multitude of compounds have been introduced to cells, including genes, antigens, and toxins.

A lipid-entrapped, polycation-condensed DNA system has been previously disclosed in U.S. Pat. No. 6,436,708 to Leone et al., ("Delivery system for gene therapy to the brain") that can exert its effect for up to ten months. This reference fails to teach or suggest a means for the selective release of genes in response to an external signal. The reference also fails to teach or suggest the release of mRNA and the synthesis of proteins within the encapsulation device. The content of U.S. Pat. No. 6,436,708 is hereby incorporated by reference into this specification.

U.S. Pat. Nos. 6,620,617; 6,475,779 and 6,262,034 to Mathiowitz et al, ("Polymeric gene delivery") discloses a gene therapy method wherein the genes to be introduced are encapsulated within a biodegradable matrix. As the matrix is slow degraded, the gene is gradually released. U.S. Pat. Nos. 6,247,720 and 6,677,313 to Mathiowitz et al., ("Method for gene therapy using nucleic acid loaded polymeric microparticles") discloses a method for orally administering gene therapy. The content of U.S. Pat. Nos. 6,620,617; 6,475,779; 6,262,034; 6,247,720; and 6,677,313 is hereby incorporated by reference into this specification.

U.S. Pat. Nos. 5,584,807 and 5,865,796 to McCabe ("Gas drive gene delivery instrument") describes the delivery of genetic material through nebulized microparticles. A variety of techniques are described which enable one to coat microparticles with a variety of substrates including DNA, RNA, and "other types of biological materials such as peptides, cytokines, hormones, or protein." McCabe also describes the effects of microparticles on an organism. "It has been found that carrier particles of a size of a few microns can enter living cells, by penetrating the cell walls thereof, without unduly adversely affecting the ability of most of the living cells to survive. In other words, the carrier particles can enter living cells without killing them, to thus deliver the biological material on the particles into the cell." The content of U.S. Pat. Nos. 5,584,807 and 5,865,796 is hereby incorporated by reference into this specification.

A similar enzymatically degradable gelatin based system is taught in U.S. Pat. Nos. 6,410,517 and 6,410,517 to Truong et al., ("Targeted gene delivery system"). The gene delivery method utilizes recognition molecules to promote target specificity. "The linkage design allows the attachment of any molecule onto the microparticle surface including antibodies, cell adhesion molecules, hormones and other cell-specific ligands." A similar disclosure may be found in U.S. Pat. No. 6,025,337 to Thuong et al, ("Solid microparticles for gene delivery").

U.S. Pat. No. 6,420,176 to Lisziewicz et al, ("Compositing for delivering DNA into antigen presenting cells") describes a gene therapy that exploits natural receptor-mediated endocytosis to introduced genes into an antigen-presenting cell. The content of U.S. Pat. Nos. 6,410,517; 6,025,337; and 6,420,176 is hereby incorporated by reference into this specification.

Sensor controlled drug delivery systems are also know to those skilled in the art. U.S. patent applications 2003/0040682 and 2003/0023187 describe systems for sampling and analysis of body fluids by non-invasively withdrawing and evaluating analytes from a biological subject and subsequently administering therapeutic agents. Additional examples of biosensors may be found in U.S. patent application 2003/0032892 wherein the device overcomes the deficiencies of a disease state when inserted into a body passage or implanted into body tissue by providing an apparatus comprised of nanodevices, microdevices and microsensors that determine changes in body conditions. The content of each of the aforementioned applications is hereby incorporated by reference into this specification.

Capsules, also known as nanospheres, nanocapsules, microspheres, or microcapsules, are known to those skilled in the art to deliver antisense oligonucleotides (Advanced Drug Delivery Reviews, v47, p 99–112, 2001). The capsule facilitates intracellular penetration and protects the oligonucleotides until they can exert their inhibitory effects. Birrenbach and Speiser (1976) first developed nanoparticles (J. Pharm. Sci. v65, pp. 1763–1766, 1976). Once biodegradable polymers were available, such capsules could be utilized for drug delivery. At that time, the research on colloidal carriers was mainly focusing on liposomes. Nanoparticles, which are more efficient drug carriers than liposomes, have since been developed (Antimicrobial Agents and Chemotherapy, v35, p 770–772, 1991). It is also known to those skilled in the art that polymers, such as poly-DL-lactic-acid-polyethylene glycol, can be used as a DNA delivery system (J. Controlled Release, v83, pp 147–155, 2002). Delivery of plasmid DNA by nanoparticles made from biodegradable polyphosphoester, poly(2-amino ethyl propylene phosphate) (PPE-EA) improves the DNA bioavailability and sustains extracellular release of the DNA (Gene Therapy, v9, pp 1254–1261, 2002).

It would be advantageous if one could control the release of a therapeutic agent such that the agent is discharged in response to a predetermined signal. One aspect of the instant invention utilizes a cantilever to control the release of such an agent.

As is known to those skilled in the art, a cantilever (also known as a microcantilever) is a microscale bar, typically ranging in size from about 1 to about 200 micrometers, that bends when subjected to a specified condition. A variety of cantilevers have been made which are responsive to numerous conditions such as, for example, specific chemicals, heat, magnetic fields, and the like.

U.S. Pat. No. 6,096,559 to Thundat et al., entitled "Micromechanical calorimetric sensor" discloses a cantilever that is sensitive to thermal changes.

U.S. Pat. No. 6,016,686 to Thundat ("Micromechanical potentiometric sensors") teaches a cantilever that is responsive to differences in potential charges on either side of the lever. U.S. Pat. No. 5,918,263 to Thundat ("Microcantilever detector for explosives") describes the use of cantilevers to detect gas molecules that have been absorbed on the surface of the lever. U.S. Pat. No. 6,525,307 to Evens et al., ("Integrated optical Interrogation of micro-structures") discloses a method for detecting the amount of bending a cantilever has undergone. U.S. Pat. No. 6,311,549 to Thundat et al., ("Micromechanical transient sensor for measuring viscosity and density of a fluid") teaches a cantilever that may be excited to resonance by vibration, thus providing a method for measuring the viscosity of a fluid. U.S. Pat. No. 5,719,324 to Thundat et al., ("Microcantilever sensor") is similar in nature. U.S. Pat. No. 6,212,939 to Thundat ("Uncoated microcantilevers as chemical sensors") describes a cantilever that is responsive to photonic energy. U.S. Pat. No. 5,908,981 to Atalar et al. ("Interdigital deflection sensor for microcantilevers) discloses a similar cantilever assembly. U.S. Pat. No. 5,998,995 to Osiander et al., ("Microelectromechanical (MEMS)-based magnetostrictive magnetometer") describes a cantilever sensitive to a magnetic field. U.S. Pat. No. 5,807,758 to Lee et al., ("Chemical and biological sensor using an ultra-sensitive force transducer") teaches a similar cantilever that is indirectly sensitized to a magnetic field. U.S. Pat. No. 5,475,318 to Marcus et al. ("Microprobe") describes a microcantilever that is thermally sensitive. As the cantilever bends in response to applied heat, the probe is moved into the appropriate position. U.S. Pat. No. 5,445,008 to Wachter et al. ("Microbar sensor") teaches the use of a microcantilever to absorb chemicals onto the surface of the cantilever. The cantilever is thus caused to oscillate. The mass of the absorbed chemicals causes the oscillation frequency to change, thus providing a method for the detection of the chemicals.

Additional cantilevers have been disclosed which sense specific chemical and/or biological analytes. Reference may be had to U.S. Pat. No. 6,523,392 to Porter et al., ("Microcantilever sensor"), U.S. Pat. No. 6,589,198 to Soltanpour et al. ("Implantable micro-pump assembly"), U.S. Pat. No. 5,643,247 to Fernandez et al., ("Microparticle switching devices for use in implantable reservoirs"), and U.S. Pat. No. 6,289,717 to Thundat et al., ("Micromechanical antibody sensor"). For additional information related to cantilevers, reference may had, for example, to U.S. patent application 2003/0010097 and U.S. Pat. Nos. 5,445,008; 5,475,318; 5,719,324; 5,908,981; 5,918,263; 5,998,995; 6,016,686; 6,096,559; 6,289,717; 6,311,549; 6,523,392; and 6,525,307. The content of U.S. Pat. Nos. 5,445,008; 5,475,318; 5,643,247; 5,719,324; 5,807,758; 5,908,981; 5,918,263; 5,998,995; 6,016,686; 6,096,559; 6,212,939; 6,289,717; 6,311,549; 6,523,392; 6,525,307; 6,589,198 and application 2003/0010097 are hereby incorporated by reference into this specification.

It is an object of this invention to provide a device for increasing the concentration of a therapeutic agent in a given environment by releasing the agent from a capsule in response to the detection of a molecule that is characteristic of a specific disease.

SUMMARY OF THE INVENTION

Disclosed is a device which employs a chemically sensitive cantilever hingably attached to a capsule. The cantilever functions as a switch which regulates the flow of particles into and/or out of the capsule. In one embodiment, the microcapsule is comprised of at least one channel. The cantilever is disposed on the surface of the microcapsule such that it covers at least one of the channels. The surface of the cantilever is comprised of a material sensitive to a predetermined substrate. The cantilever bends in response to the presence of this substrate on the cantilever. This bending exposes the microcapsule channel(s) to the environment outside of the microcapsule. In this manner, the contents of the microcapsule are released. The contents generally include therapeutic agents designed to treat a disease. Suitable target diseases include, but are not limited to, Alzheimer's disease, Parkinson's disease, Huntington's disease, amyotrophic lateral sclerosis and cancer.

The technique of the invention is advantageous because it triggers a therapeutic treatment as a result of a detected disease condition. As a result of the invention, a therapeutic compound is not continuously released at a steady rate. Rather doses of a therapeutic agent are released in relatively high concentrations when a disease condition is detected.

BRIEF DESCRIPTION OF THE DRAWINGS

The invention will be described by reference to the following drawings, in which like numerals refer to like elements, and in which.

Figure 1:
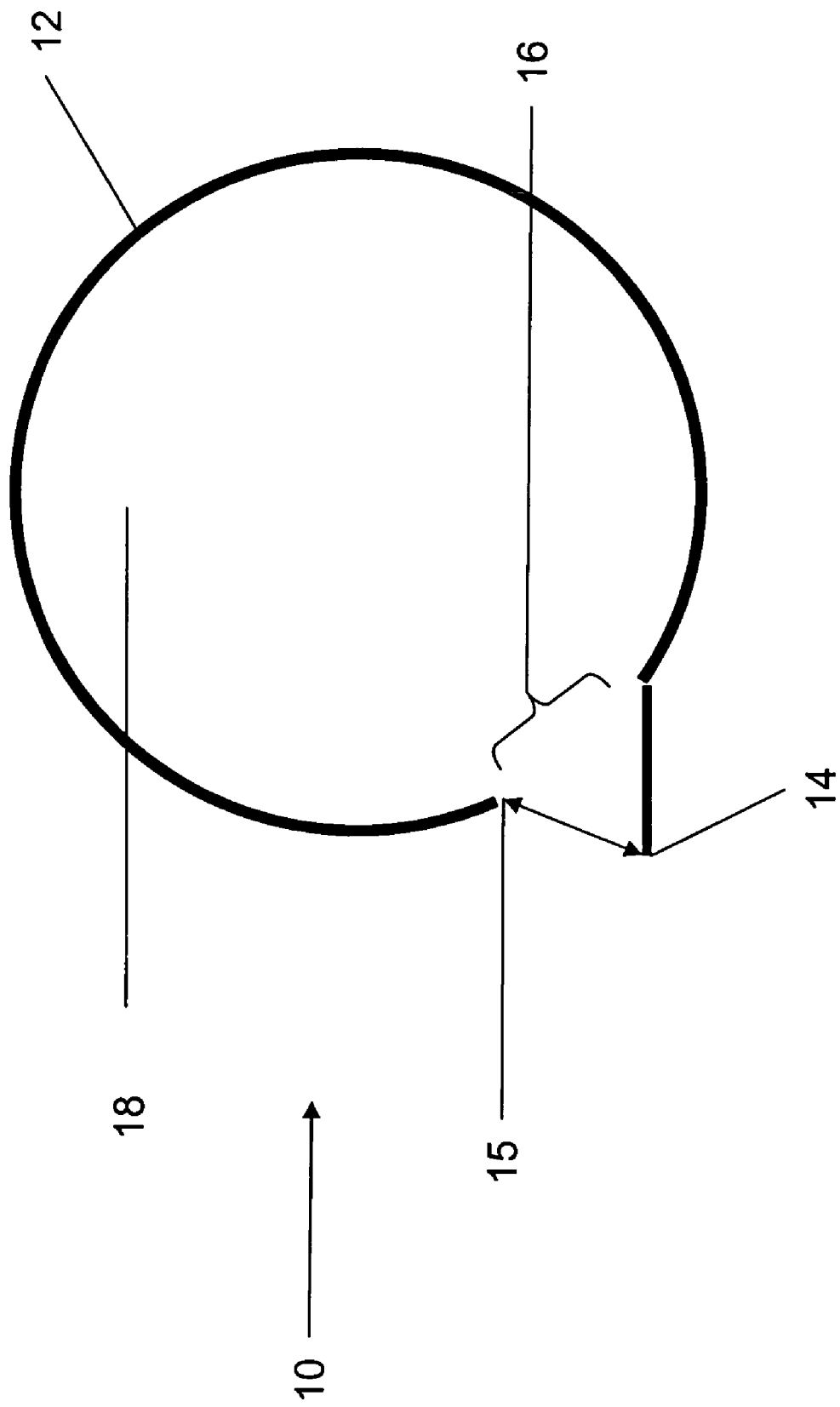
FIG. 1 is a section view of one embodiment of the invention.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention as defined by the appended claims.

DESCRIPTION OF THE PREFERRED EMBODIMENTS

For a general understanding of the present invention, reference is made to the drawings. In the drawings, like reference numerals have been used throughout to designate identical elements.

In the embodiment depicted in FIG. 1, device 10 is comprised of capsule 12 and cantilever 14 (also referred to as a microcantilever). As used in this specification, the term cantilever (or microcantilever or nanocantilever) is defined as a microscale bar which is sensitive to chemical stimuli. Such bars typically range in size from about 1 micrometer to about 200 micrometers. Reference may be had to U.S. Pat. Nos. 6,523,392; 6,589,198; 5,643,247; 6,289,717 and the like. The content of U.S. Pat. Nos. 6,523,392; 6,589,198; 5,643,247; and 6,289,717 is hereby incorporated by reference into this specification. Capsule 12 is comprised of channel 16 and cavity 18. The term "channel", as used in this specification, refers to an opening in the capsule through which particle flow between cavity 18 and the outside environment is regulated by action of the cantilever. In the embodiment depicted in FIG. 1, capsule 12 is generally spherical. As would be apparent to those skilled in the art, other shapes are suitable (cylinders, squares, and the like). Cantilever 14 is disposed over channel 16 and the channel is at least partially obstructed. In this manner, the flow of particles into and out of chamber 18 via channel 16 is inhibited when cantilever 14 is in the closed position. Conversely, particle flow into and out of cavity 18 is more freely permitted when cantilever 14 is in the open position. In the embodiment depicted in FIG. 1, cantilever 14 is in the open position, but is adapted to reversibly move in either direction of arrow 15 to open and close channel 16.

Materials suitable for the capsules include non-biodegradable materials, including but not limited to, polymers, ghost cells, microspheres, microparticles, and the like. In one embodiment, the capsule is the microparticle disclosed and claimed in U.S. Pat. No. 5,559,202 to Yoshikawa ("Bowl-shaped microparticle and production thereof"). In another embodiment, the capsule is that disclosed and claimed in U.S. Pat. No. 5,770,076 to Chu et al., ("Micromachined capsules having a porous membranes and bulk supports"). In yet another embodiment, the capsule is comprised of the microparticles disclosed in U.S. Pat. No. 5,643,247 to Fernandez et al., ("Microparticle switching devices for use in implantable reservoirs"). In another embodiment, the capsule is comprised of the metalized microtubules disclosed in "Three-dimensional metallization of microtubules" in Thin Solid Films, vol 305, pp 248–253 (1997). In another embodiment, the capsule is comprised of carbon nanotubes. In another embodiment, the capsule is comprised of silicon. In another embodiment, the capsule is comprised of micromachined silicon nitride. The content of U.S. Pat. Nos. 5,559,202; 5,770,076; and 5,643,247 is hereby incorporated by reference into this specification.

In one embodiment, the capsule is comprised of polymer-like micelles formed by surfactants and micelles- vesicles-liposomes via block copolymers. The formation of long micelles is observed in solutions of ionic surfactant under certain conditions. In one embodiment, the physical properties of such micelles are modified by changing the surfactant molecular structure, type of counter-ion or the amount of added salt so as to alter the size, flexibility and interactions of the micelles. This, in turn, gives marked effects on the macroscopic rheological properties.

In aqueous solutions, amphiphilic block copolymers comprising a hydrophobic and a hydrophilic polymer block form vesicles with a bilayer of block copolymers similar to cell membranes. They also form spherical or cylindrical micelles with a hydrophobic micellar core and a water-swollen micellar shell. These structures are not only interesting in their own right, but are used in materials science for pharmaceutical applications and for the preparation of nanostructured materials such as semiconductors, noble metals, and mesoporous ceramics. Reference may be had to an article by Feyerabend available on the internet [online], [retrieved on 2004-05-24]. Retrieved from the Internet <URL:http://www.gkss.de/pages.php?page=w_abt_wfs_general.html&language=d&version=g>. In another embodiment, the capsule is comprised of nanotubes or metalized nanotubes. Reference may be had to an article by Zaric et al. entitled "Optical signatures of the Aharonov-Bohm Phase in Single-Walled Carbon Nanotubes" (Science v304, p1129, 2004), and Coskun et al. entitled "h/e Magnetic Flux Modulation of the Energy Gap in Nanotube Quantum Dots" (Science, v304, p1132, 2004) and the like.

The use of cantilevers as valves has been previously disclosed in U.S. Pat. No. 6,589,198 to Soltanpour et al. ("Implantable micro-pump assembly"). The cantilever of U.S. Pat. No. 6,589,198 is a simple mechanical lever, and is not chemically sensitive. Other microvalves are known to those skilled in the art. Reference may be had to U.S. Pat. Nos. 5,417,235; 5,322,258; 5,333,831; 5,309,943; 5,238,223; 5,197,517; 5,180,623; 5,176,358; 5,029,805; 6,589,198 and 5,161,774. The content of each of these patents is hereby incorporated by reference into this specification. Other cantilevers have been developed which are chemically sensitive. Throughout this specification the phrase "chemically sensitive cantilever" is given special meaning. This refers to a cantilever which has been rendered sensitive to a predetermined molecule, usually by coating the cantilever with a layer of receptor molecules. As the concentration of bound molecules on the cantilever surface increases, the cantilever is caused to bend. Reference may be had to U.S. Pat. Nos. 6,523,392 to Porter et al., ("Microcantilever sensor") and 6,289,717 to Thundat et al., ("Micromechanical antibody sensor"). As is disclosed in U.S. Pat. No. 6,289,717, Thundat provides " . . . a cantilever with one of its surfaces coated with specific binding partners such as antibody or antigen molecules, or with specific binding peptides identified from display libraries, while the other surface is covered with a different, possibly inert, material. As long as the amount of adsorption is different on the opposing surfaces, or there are different interactions of monitored molecules on opposing surfaces, there will be a differential stress. Since the cantilever thickness is very small, an antibody-antigen (Ab-Ag) type of interaction is manifested as changes in the differential surface stress of the microcantilever surface . . . these changes in differential surface stress manifest themselves as changes in cantilever deflection which can be measured with sub-angstrom sensitivity." Similarly, an article entitled "Micro and Nanocantilever Sensors" by P. G. Datskos, T. Thundat, and N. V. Lavrik (Encyclopedia of Nanoscience and Nanotechnology, pages 1–10) discloses that "chemical selectivity is obtained by utilizing chemically selective layers such as polymeric films, self-assembled monolayers, or antibody-antigen layers. Regeneration of the sensor originates from thermodynamics . . . thin microcantilevers also undergo bending due to mechanical forces generated by molecular adsorption, one of the most overlooked yet fascinating aspects of adsorption." Additionally, this article discloses that cantilevers with dimensions of 0.8 to 2 μm in length, 50 to 500 nm in width, and 25 to 100 nm in thickness have been fabricated. The content of U.S. Pat. Nos. 6,523,392; and 6,289,717 is hereby incorporated by reference into this specification.

Figure 2:
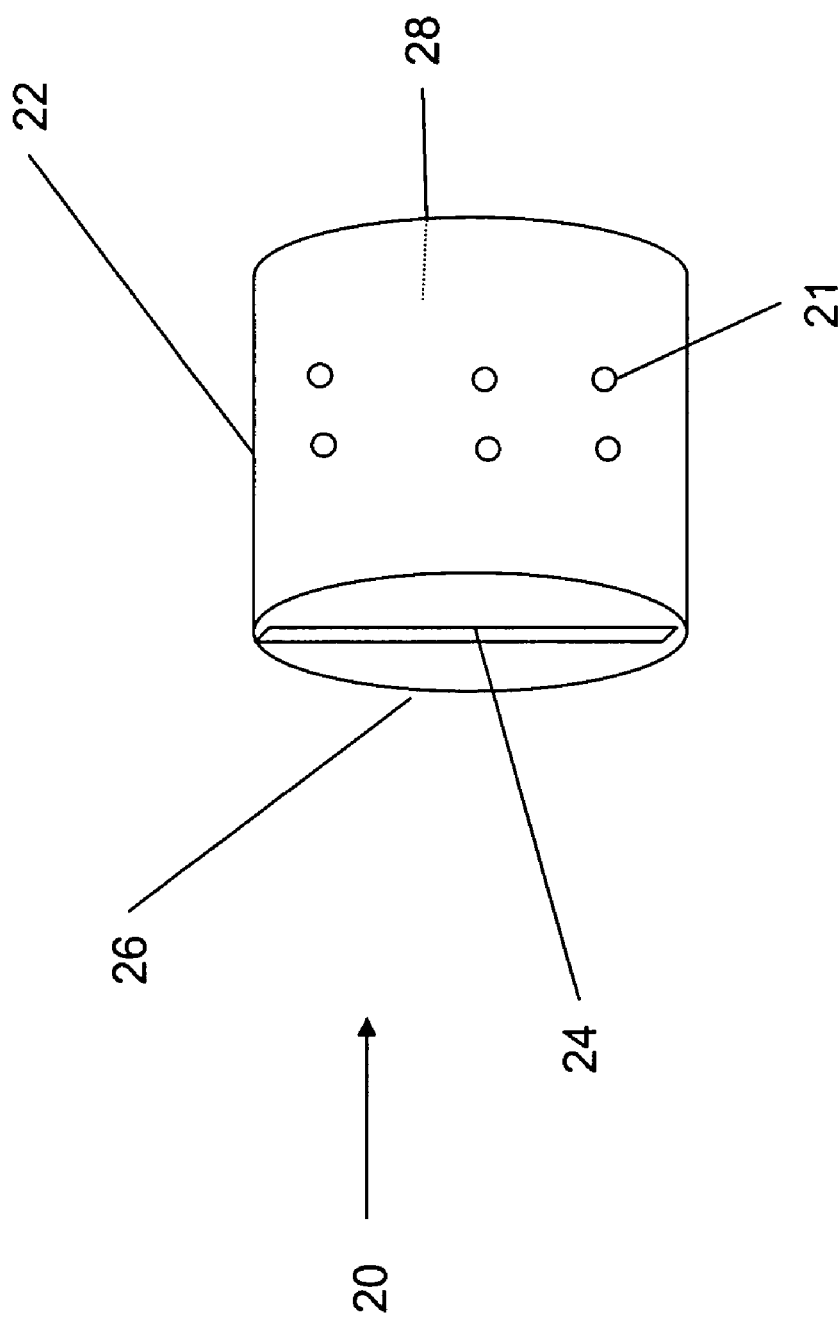
FIG. 2 is a perspective view of one embodiment of the invention.

FIG. 2 depicts another embodiment of the instant invention. In FIG. 2, device 20 is comprised of capsule 22 and cantilever 24 which at least partially obstructs channel 26. Channel 26 is fluidly connected to inner cavity 28. In the embodiment that is depicted, cantilever 24 is in the closed position. Device 20 further comprises pores 21, wherein the pores have a diameter less than that of channel 26. Pores 21 thus allow for the flow of small particles into and out of cavity 28. The diameter of pores 21 is selected to allow the flow of small molecules through the pores (amino acids, for example), but restrict the flow of larger molecules such as proteins and/or mRNA. It is well known to those skilled in the art that amino acids, for example, will diffuse through pores as small as a few nanometers, whereas proteins require larger pores. In one embodiment, the diameter of pore 21 is between about 8 nanometer and 20 nanometers and preferably between 10 and 15 nanometers. The capsule 22 depicted in FIG. 2 is a cylinder. As would be apparent to those skilled in the art, other capsule shapes may be employed.

Figure 3:
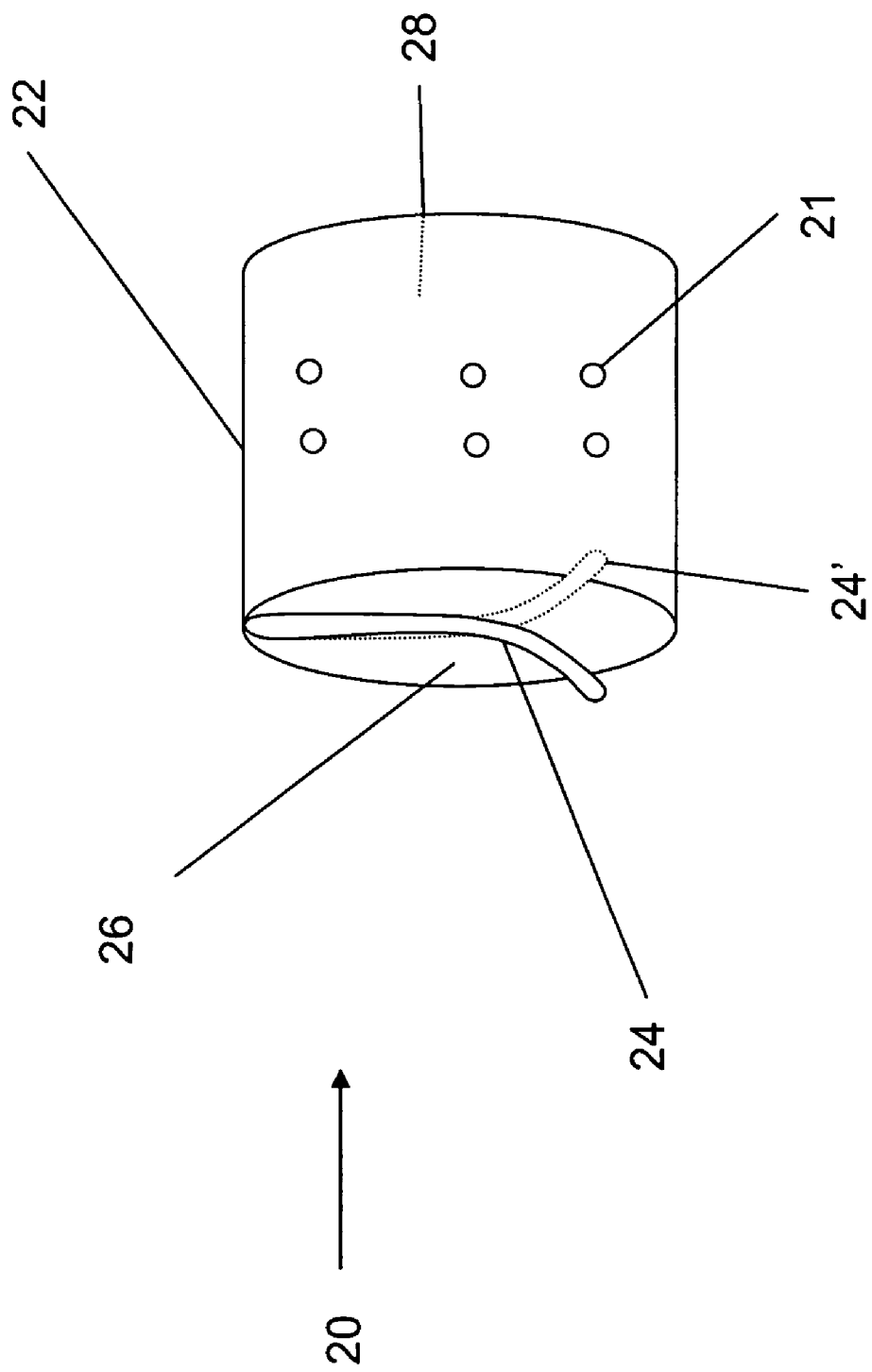
FIG. 3 is a perspective view of an embodiment similar to that depicted in FIG. 2, wherein cantilever motion is illustrated.

FIG. 3 is another view of the invention depicted in FIG. 2 wherein the cantilever is shown in the open position. Device 20 is comprised of capsule 22, cantilever 24, channel 26, cavity 28, and pores 21. In the embodiment depicted, cantilever 24 is hingably attached to capsule 22 and is in the open position. As is apparent from this figure, cantilever 24 need not be fully open to permit the flow of particles through channel 26. In one embodiment, channel 26 is substantially blocked by cantilever 24 such that particle flow is inhibited. Depending on the particulate size, a partial opening of cantilever 24 may be sufficient to allow the escape of the aforementioned particles. Additionally or alternatively, cantilever 24 may deflect in such a way that it is displaced inward. Reference may be had to element 24' shown in FIG. 3.

Figure 4:
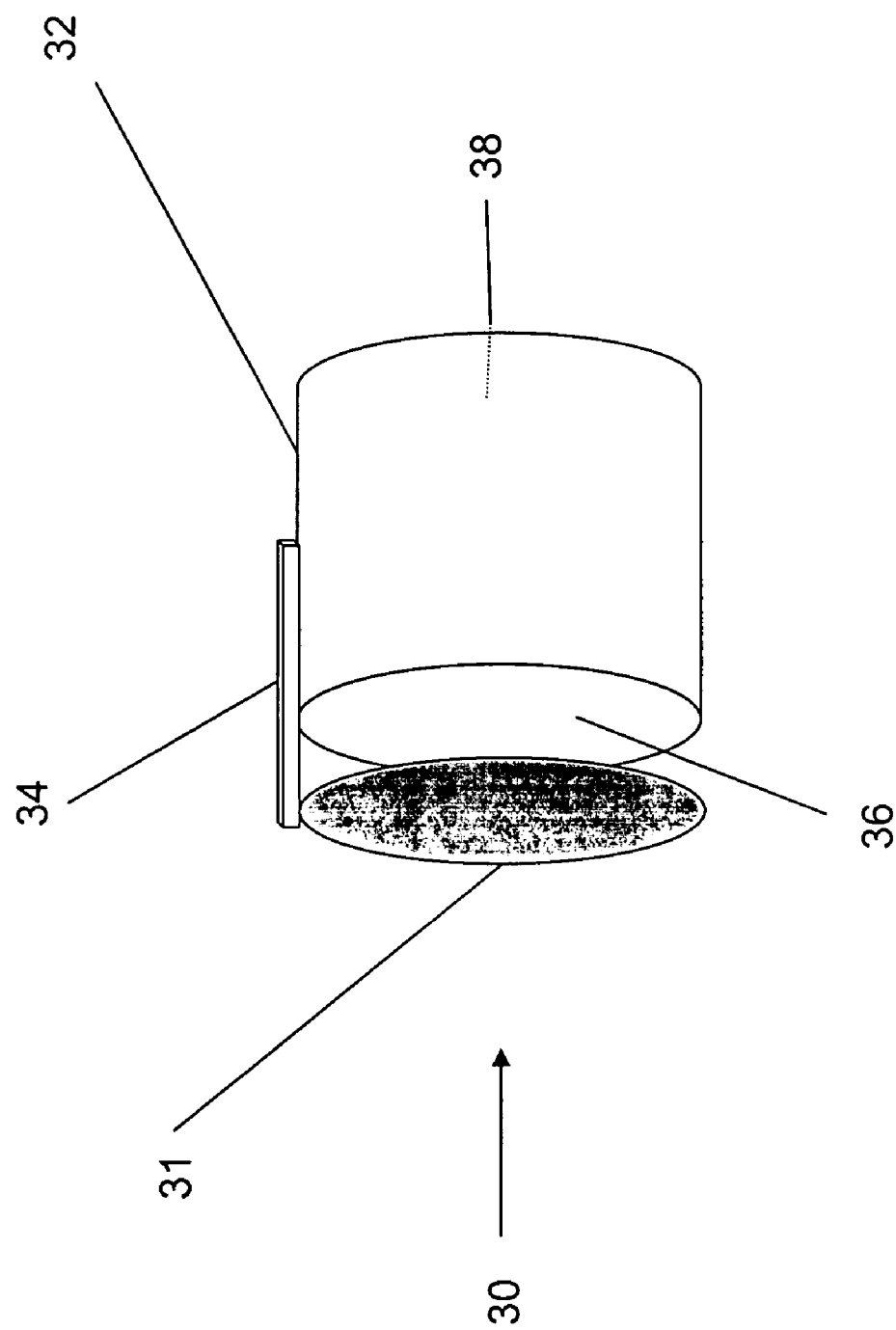
FIG. 4 is a perspective view of another embodiment of the invention.

FIG. 4 is another embodiment of the invention that depicts another method of using a cantilever to restrict the flow of particles through a channel. In the embodiment depicted, device 30 is comprised of capsule 32, cantilever 34, channel 36, inner cavity 38, and cover 31. The device is configured such that cantilever 34 hingably connects capsule 32 to cover 31. In the embodiment depicted, cantilever 34 is in the closed position. For the sake of clarity, the gap between channel 36 and cover 31 has been exaggerated. As would be apparent to those skilled in the art, the gap between channel 36 and cover 31 need not be zero. In one embodiment of the device, such a gap is present so as to allow for the diffusion of small molecules into and out of inner cavity 38.

Figure 5:
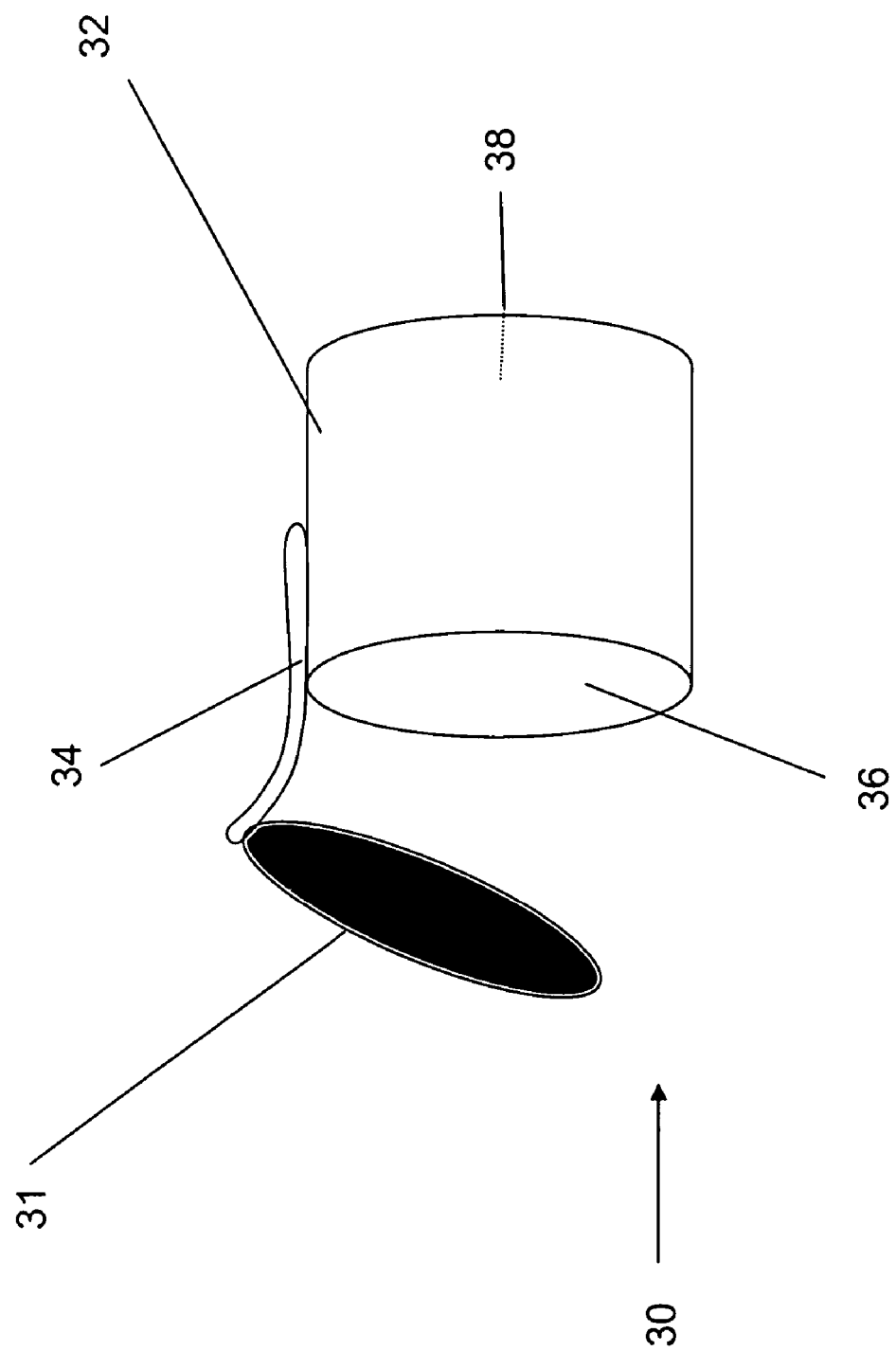
FIG. 5 is a perspective view of an embodiment similar to that depicted in FIG. 4, wherein cantilever motion is illustrated, FIGS. 6, including 6A, 6B, and 6C are sectional views depicting three embodiments of cantilever configurations.

FIG. 5 shows another view of the invention depicted in FIG. 4 wherein the cantilever 34 is in the open position. In the embodiment depicted, device 30 is comprised of capsule 32, cantilever 34, channel 36, inner cavity 38, and cover 31. The device is configured such that cantilever 34 connects capsule 32 to cover 31. In the embodiment depicted, cantilever 34 is in the open position.

FIG. 6 depicts several cantilever arrangements of the invention. Each of FIG. 6A, FIG. 6B, and FIG. 6C depict end views of devices similar to device 20 shown in FIG. 2 and FIG. 3. In the embodiment depicted in FIG. 6A, a single cantilever 24 is employed to cover channel 26. FIG. 6B shows the use of multiple cantilevers 24 to cover channel 26. It is clear from these figures that the embodiment depicted in FIG. 6A would allow the passage of relatively large molecules through channel 26. By contrast, the molecules would have to be much smaller to pass through channel 26 of the embodiment depicted in FIG. 6B. Similarly, the embodiment depicted in FIG. 6C, in addition to utilizing cantilever 24, also utilizes blocking members 25 to restrict the size of channel 26.

Figure 7:
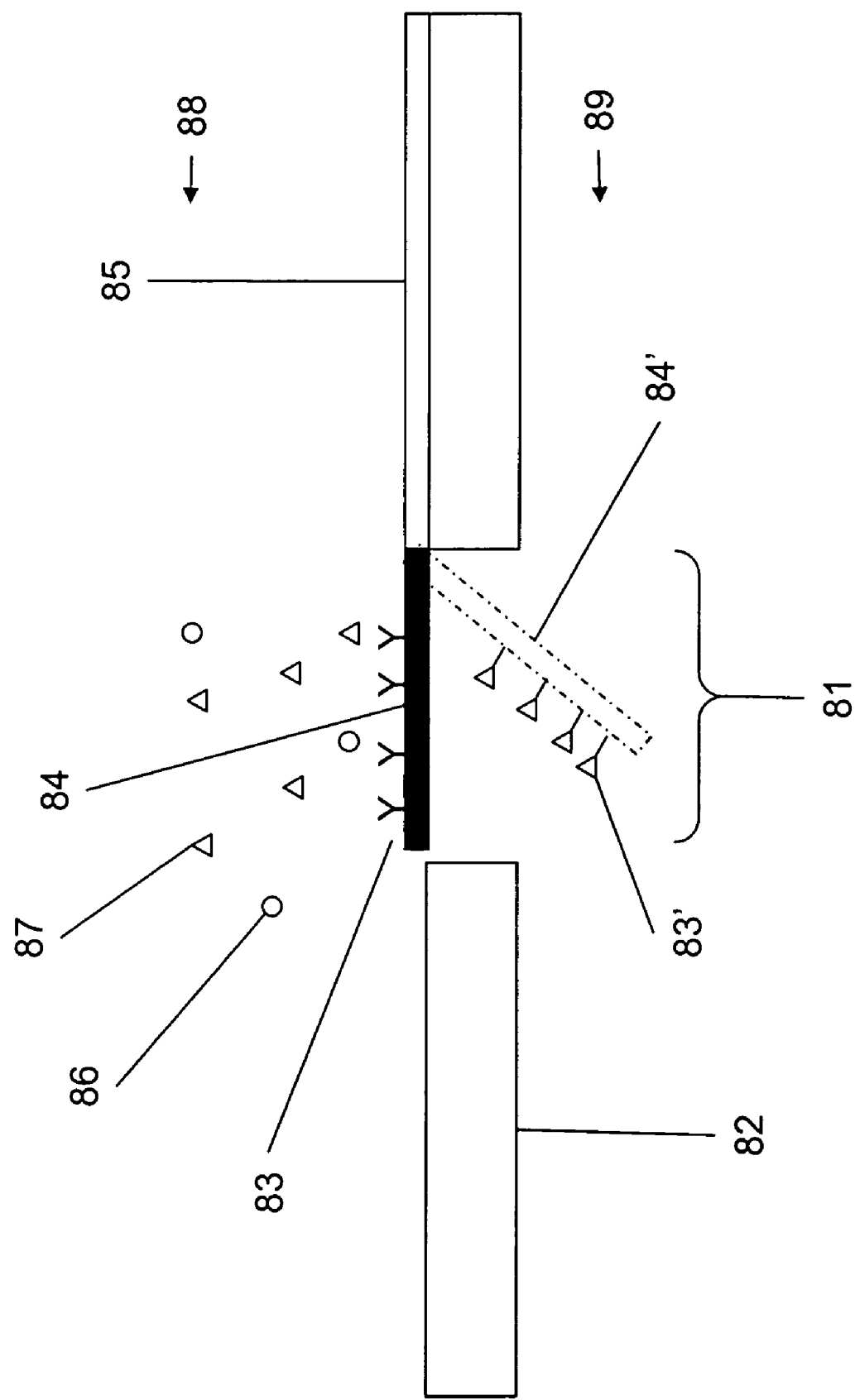
FIGS. 7, 8, and 9 are sectional views illustrating a chemically sensitive cantilever and its motions.

FIG. 7 depicts a side view of a portion of one embodiment of a capsule wherein a cantilever serves to regulate the flow of particles through a channel. Shown in FIG. 7 are the wall 82 of the capsule (not shown) comprising wall 85 and channel 81. Contiguous with wall 85 is cantilever 84, which is hingably attached to the capsule (not shown). Disposed on one surface of cantilever 84 are receptor particles 83. Receptor particles 83 are exposed to the environment 88. In one embodiment environment 88 is the inner cavity of the capsule while environment 89 is the outside environment. In another embodiment, environment 88 is the outside environment, while 89 is the inner cavity of the capsule. Receptor particles 83 possess a binding site such that particles 87 will reversibly bind, but other particles, such as 86 will not bind. As more particles 87 bind in the active site of receptor particle 83, cantilever 83 is slowly bent into a position such as 83' (or bent in the other direction), thus opening channel 81. As would be apparent to those skilled in the art, wall 85 may be the inner wall of the capsule or the outer wall.

Figures 8, 8A, 8B, 8C:
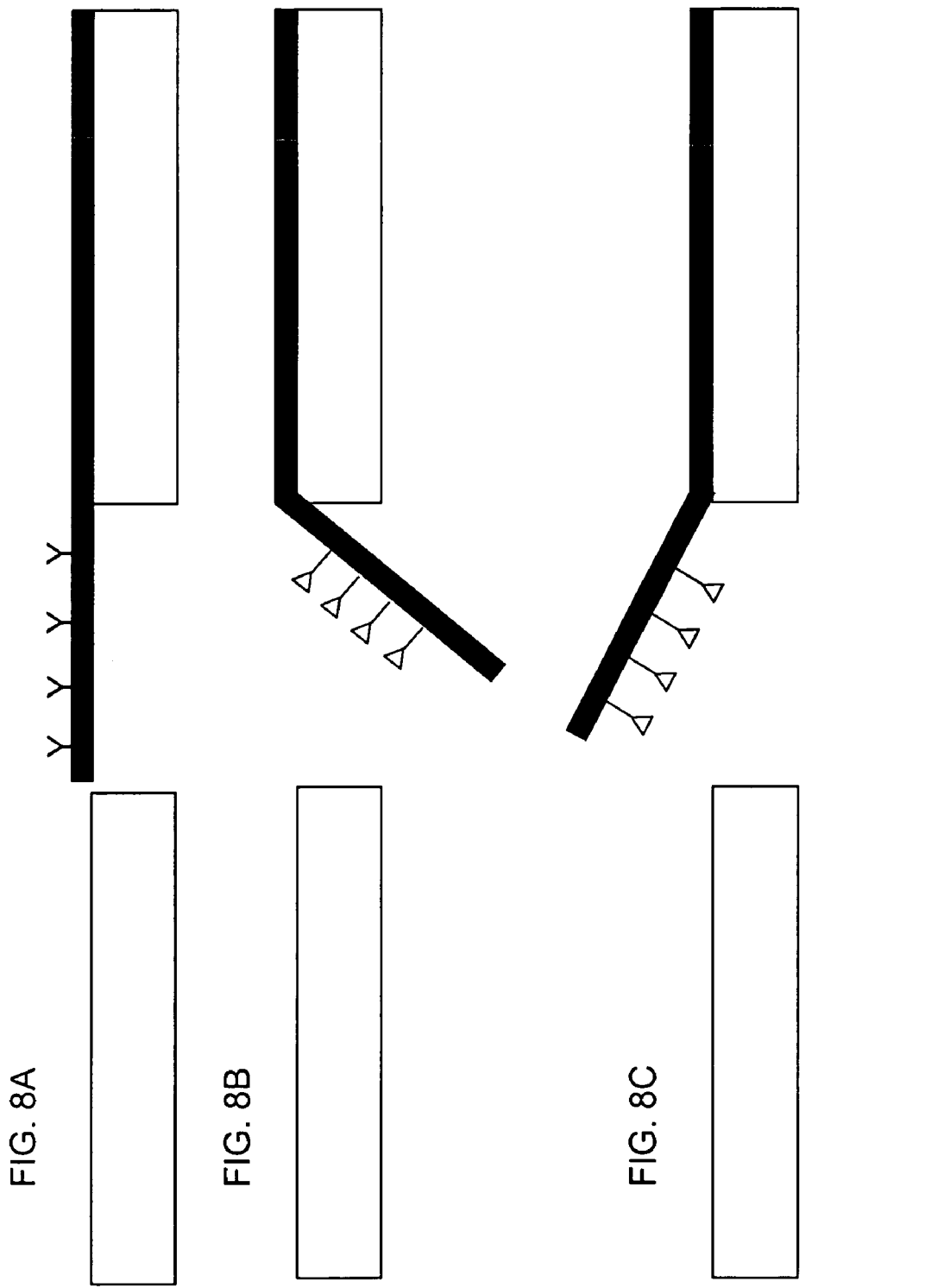

FIG. 8 illustrates several modes of cantilever hingability which depend on the positing of the receptor molecules. FIG. 8A depicts a cantilever in the closed position. FIG. 8B and FIG. 8C show cantilever operation in opposite directions depending on which surface of the cantilever is coated with the receptor particles. Moreover, cantilevers may open into or away from the inside of the capsule. One need not have an unevenly coated cantilever for the invention to be operable.

Figure 9:
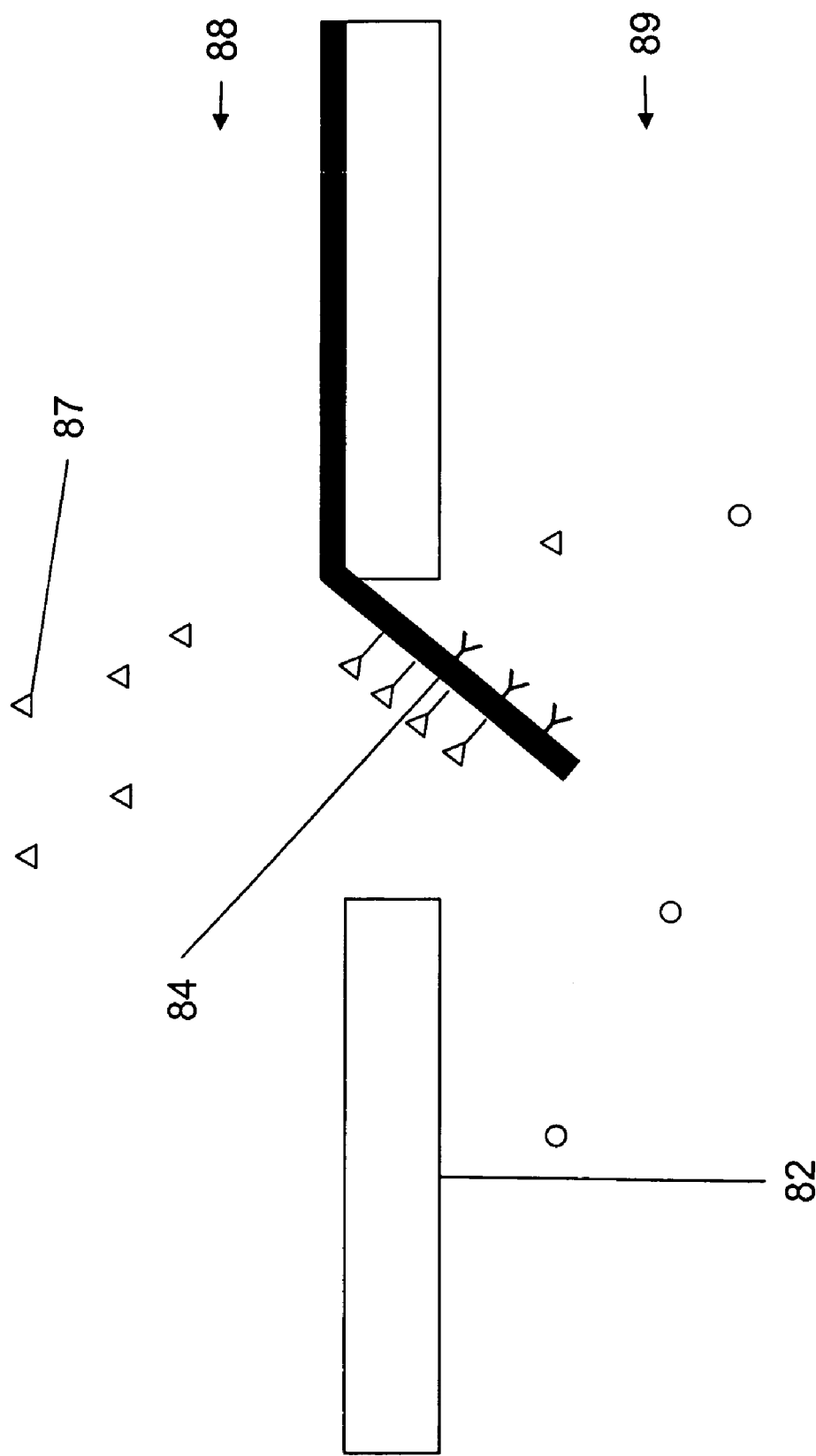

FIG. 9 depicts one embodiment of the invention that illustrates an unevenly coated cantilever. In one embodiment cantilever 84 bends in response to a difference in concentration of molecules 87 on either side of wall 82. In the embodiment depicted in FIG. 9, the concentration of molecules 87 is higher in environment 88 than it is in environment 89. As such, cantilever 84 bends, even though cantilever 84 is evenly coated with receptor molecules 84.

A wide variety of coatings are suitable as biosensors. U.S. Pat. No. 6,289,717 teaches that Enzyme-Linked Immunosorbent Assay (ELISA) techniques may be used to coat cantilevers with agents (e.g., antibodies) that render the cantilever sensitive to chemical compounds. The content of U.S. Pat. No. 6,289,717 is hereby incorporated by reference into this specification. In one embodiment, the cantilever surface is coated with motor proteins that render the cantilever sensitive to microtubules. In one such embodiment, the motor protein is kinesin. Such kinesin laden surfaces are known to those skilled in the art. Reference may be had to an article by Haw published on the internet on Sep. 19, 2001 entitled "Arrows point to Nanotech's future." Additional reference may be had to Hess et al. (Nano Letters, v1, p235), Hiratsuka et a. (Biophysical Journal, v81, p1555), and the like. In another embodiment, the surface differentiates normal from abnormal microtubules. As is apparent to those skilled in the art, defective microtubules interact differently with the kinesin surface. In some disease states, defective microtubules proliferate at a rate exceeding normal microtubules. For such diseases, a cantilever is coated with a layer of motor proteins which will cause the bending of a cantilever when the microtubule abundance exceeds a certain value. Thus, a kinesin surface allows for detection of abnormal microtubules in the presence of normal microtubules.

Prior art acknowledges a relationship between microtubules and disease U.S. Pat. Nos. 6,498,257; 6,303,358; 6,297,035; 6,277,963; 5,994,084; 5,914,261; 5,872,006; 5,776,751; 5,760,092; and 5,595,904. The content of each of these patents is hereby incorporated by reference into this specification. A comprehensive list of diseases that are due to abnormalities in microtubules or microtubules binding to other proteins has not been elucidated, but it is clear that many disorders share this common underlying feature. The proteomics of such disease states are only beginning to be understood. Genetic expression studies have shown down-regulation of high molecular weight microtubule associated protein-2 (MAP-2) in post mortem Alzheimer's disease brain samples. Tau and huntingtin proteins are also known to bind to microtubules. Abnormalities in these, and other, proteins provide the probable molecular bases of Alzheimer's disease and Hungtington's disease (J. Cell Science, v115, p941–948, 2002). Altered patterns of tau and MAP-2 have also been demonstrated in Parkinson's disease and in a mouse model of amyotrophic lateral sclerosis (Neuroscience Letters v306, pp137–140, 2001). In addition, cell mitosis is known to depend on microtubules, and some anti-cancer drugs exert their effects through inhibition of microtubule-mediated cell division (Molecular Pharmacology, v63, pp799–807, 2003).

As is known to those skilled in the art, the binding patterns of microtubule associated proteins (e.g., tau, MAP-2, huntingtin) are altered in diseased cells as compared to the binding patterns of healthy cells. Reference may be had, for example, to U.S. Pat. No. 6,498,257, the contents of which are hereby incorporated by reference. Microtubules contain a surface morphology which can be detected. As is apparent to one skilled in the art, the surface morphology of microtubules can be directly analyzed experimentally using techniques such as scanning tunneling microscopy (STM) and atomic force microscopy (AFM). See, for example, an article available on the internet [online], [retrieved on 2004-05-24]. Retrieved from the Internet <URL:http://www.bio-physik.uni-bremen.de/radmacher/publications/microtubule.html>, and Maaloum et a. (J. Cell Sci. v107, p3127-31, 1994).

In another embodiment, the cantilever is coated with a layer of receptor particles (e.g., antibodies) which bind to sensed particles. In one such embodiment, the sensed particles are hyperphosphorylated tau, and the receptor particles are those disclosed in the article by Hu et al. entitled "Levels of Nonphosphorylated and Phosphorylated Tau in Cerebrospinal Fluid of Alzheimer's Disease Patients" (Am. J. of Pathology, v160, p1269, 2002). Altered levels of hyperphosphorylated tau have been previously linked to Alzheimer's disease, and thus serve as an indicator of such disease. In another embodiment, altered levels of metals are detected which are indicative of a diseased state. Reference may be had to the article by Sayre et al. entitled "In Situ Oxidative Catalysis by Neurofibrillary Tangles and Senile Plaques in Alzheimer's disease: A Central Role for Bound Transition Metals" (J. of Neurochemistry, v74, p270, 2000). In yet another embodiment, decreased levels of microtubules are detected using surface plasmon resonance technology. Reference may be had to Schuessler et al. "Surface plasmon resonance study of the actin-myosin sarcomeric complex and tubulin dimmers" (J. of Modern Optics, vol 50, p2381, 2003), Mershin et al., "Tubulin dipole moment, dielectric constant and quantum behavior: computer simulations, experimental results and suggestions", [online], [retrieved on 2004-05-24]. Retrieved from the Internet <URL:http://arxiv.org/abs/physics/ 0402053>, U.S. Pat. Nos. 6,730,269; 6,730,487; and 6,738,141. The content of U.S. Pat. Nos. 6,730,269; 6,730,487; and 6,738,141 is hereby incorporated by reference into this specification.

In one embodiment, the receptor particles are electronically complimentary to the microtubules. Microtubules have negatively charged protrusions on the C-termini of their tubulin subunits. In one embodiment, the biosensor has positively charged sites that interact with these negatively charged protrusions along microtubules. In this embodiment, there is a complementary match between the biosensor surface properties and the C-termini of microtubules, thereby enabling preferential interactions with C-termini of microtubules in defective cells as compared to those in healthy cells. In one such embodiment, the exposed surface of the biosensor will have positively charged basic amino acids, (i.e. lysine, arginine, histidine), and hence will bind readily to the predominantly negatively charged microtubule surfaces. In one embodiment, the biosensor comprises the gold-nanotube membranes disclosed by Lee and Martin (J. Am. Chem. Soc. v124, p11850-1). Similarly, U.S. patent application 2003/0026754 teaches a method for producing stable dispersions of single-walled carbon nanotube structures in aqueous solutions by coating the structures and increasing the surface interaction between the structures and water. In one embodiment of the invention, the interaction or binding between the biosensor and the defective microtubule is strong enough to activate the cantilever, but weak enough to enable the device to become dislodged and be free to interact at another site in the cell.

The biosensor need not directly detect molecular changes within a cell, as such internal changes often have an extracellular effect. Reference may be had to U.S. Pat. No. 6,277,963 and patent application 2003/0008335A1, the content of which are hereby incorporated by reference into this specification. In one embodiment, the device is disposed outside of a cell, but is in contact with the cell wall. In this manner, the biosensor may detect a variety of extracellular effects, such as alternations in the cytoskeleton caused by microtubules.

In one embodiment, the cantilever is coated with a biosensitive material that is sensitive to receptor particles. U.S. patent application 2003/0008335 describes a Quartz Crystal Microbalance piezoelectric biosensor utilizing living endothelial cells as the biological signal transduction element. This biosensor can be used for the study of endothelial cell attachment and to detect cytoskeletal alterations in real time for the purpose of identification or screening of classes of biologically active drugs or biological macromolecules that affect cellular attachment. The content of this application is hereby incorporated by reference into this specification.

Biosensors that detect biological analytes (i.e. receptor particles) using a microfabricated electrochemical device are known to those skilled in the art. Reference may be had to U.S. patent application 2002/0123048, the contents of which are hereby incorporated by reference. In one embodiment, antibodies are detected. In one such embodiment, the antibodies are related to cancer. In another embodiment, the microcantilever detects abnormalities related to microtubules, including abnormal protein binding patterns. In yet another embodiment, a therapeutic agent is detected.

Figure 10:
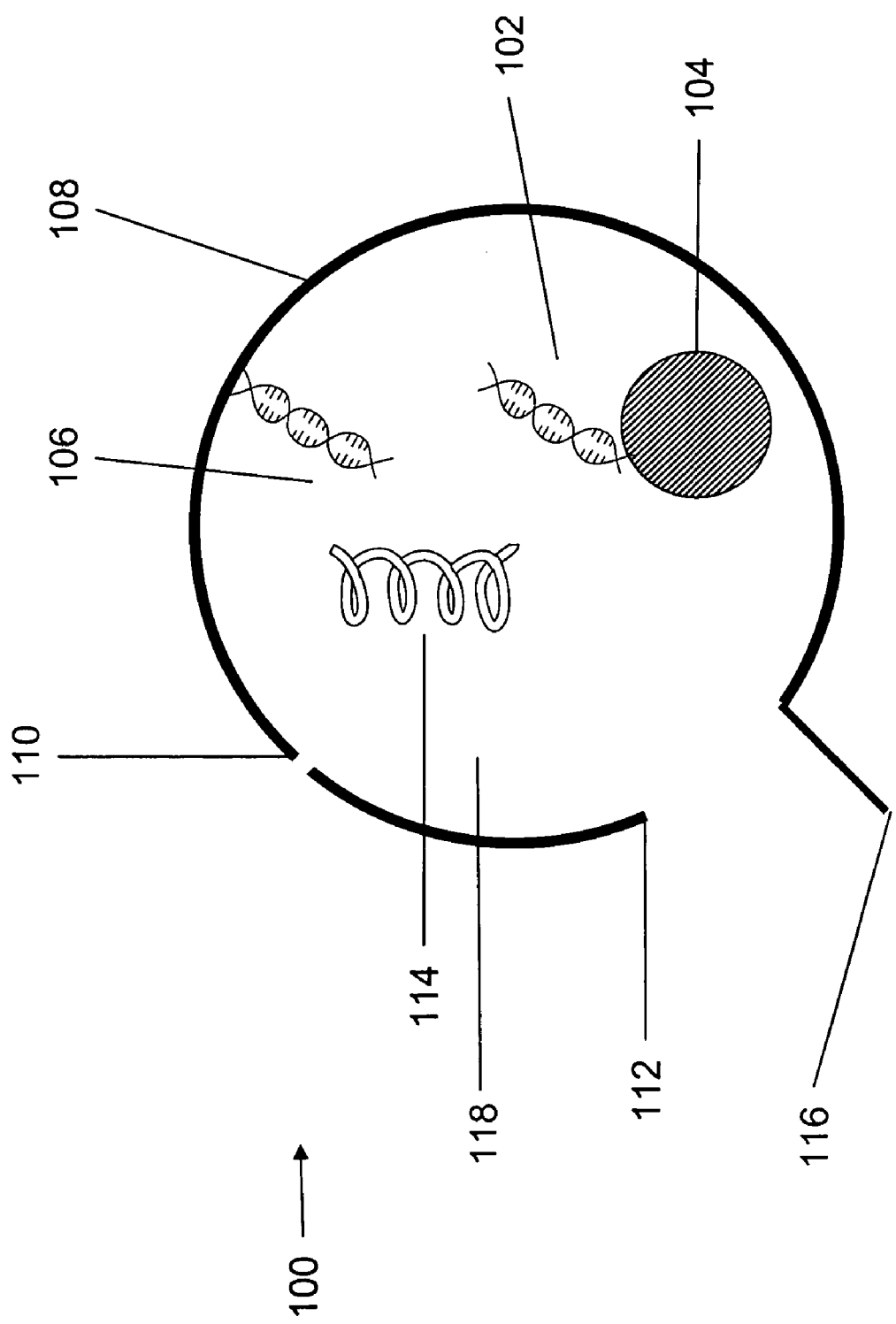
FIG. 10 is a sectional view of one embodiment of the invention, wherein mRNA is generated.

In the embodiment depicted in FIG. 10, when the cantilever 116 detects microtubules altered by the proteomics of the particular disease state, cantilever 116 hingably opens to release mRNA 114. In another embodiment, cantilever 116 opens when it detects hyperphosphorylated tau.

In one embodiment, the cantilever of the instant invention does not fully block the channel. In this embodiment, a partial obstruction is sufficient to reduce the rate of flow of particles through the channel. When the cantilever detects the requisite condition and opens the channel, the particles will be released at a higher rate than when the channel is closed.

In another embodiment, the cantilever is sensitized to particles that are located within the cavity. When sufficient concentration of particles accumulates within the cavity, the cantilever will open and release the particles. In another embodiment, the cantilever is sensitized to particles that are located external to the cavity. When sufficient concentration of particles accumulates external to the cavity, the cantilever will open and release the therapeutic particles that are contained within the cavity.

In the embodiment depicted in FIG. 10, DNA is implanted within the cell which allows for the transcription of mRNA. This mRNA is then released in high concentrations when the cantilever is triggered. In one embodiment, the DNA 106 is attached to the inner wall of the capsule 108. In another embodiment depicted in FIG. 10, DNA 102 is trapped within capsule 108 by attachment to microparticles 104 which are too large to pass through pores 110 and channel 112. Methods for attaching DNA to surfaces are well known in the art. Reference may be had to U.S. Pat. No. 6,713,272 (Attachment of biomolecules to hydrophobic surfaces), U.S. Pat. No. 6,660,533 (Attaching a biological molecule to a support surface), U.S. Pat. No. 6,548,021 (Surface-bound, double-stranded DNA protein array), U.S. Pat. No. 6,528,167 (Porous hybrid particles with organic groups removed from the surface), U.S. Pat. No. 6,326,489 ("Surface-bound, bimolecular, double-stranded DNA arrays), U.S. Pat. No. 5,858,653 (Reagent and method for attaching target molecules to a surface), U.S. Pat. No. 5,770,722 (Surface-bound, unimolecular, double-stranded DNA) and the like. The content of each of the aforementioned patents is hereby incorporated by reference into this specification. The nucleotide base pairs needed to transcribe mRNA are known to pass through a pore size of just a few nanometers. Reference may be had to Muthukumar, "Polymer escape through a nanopore" J. Chem. Phys. v18, p5174–5184, 2003; Kong, "Modeling of polynucleotide translocation through protein pores and nanotubes", Electrophoresis v23, p2697–2703, 2002, Kustanovich et al., Biophysical Journal, v86, p2008, 2004 ("Metastable Network Model of Protein Transport through Nuclear pores") and the like. Pores 110 are of such a size to allow nucleotides and the like to diffuse into cavity 118, but not allow the exodus of a significant amount of mRNA 114. Numerous methods for controlling the pore size of microparticles are known. For example, reference may be had to U.S. Pat. No. 5,770,076 to Chu et al, ("Micromachined capsules having porous membranes and bulk supports). The content of this patent is hereby incorporated by reference into this specification. In the embodiment depicted in FIG. 10, nucleotide base pairs (not shown) diffuse into inner cavity 118 and interact with DNA 106 and/or DNA 102. As is well known in the art, this interaction produces mRNA 114. When cantilever 116 opens, mRNA is released through channel 112. In one embodiment, the device is operative within a cell for relatively long duration. In another embodiment, the device is located outside of a cell. In the embodiment depicted in FIG. 10, one may pre-select the DNA segment to be used, as well as the biosensor the cantilever is coated with so as to detect and treat a specific disease.

As an example, we describe one such device containing appropriate DNA to treat Alzheimer's disease. As is known to those skilled in the art, the proteomics of Alzheimer's disease is such that microtubule-associated protein-2 (MAP-2) expression is reduced (DNA and Cell Biology, v20, p683–695, 2001, note erratum in v21, p241, 2002). In one embodiment, the DNA is selected so as to increase MAP-2 in cells affected with Alzheimer's disease pathology and having reduced MAP-2 gene expression. In another embodiment, the nanodevice is filled with deoxyribonucleic acid (DNA) which codes for other proteins that normally bind to the microtubule, but are deficient in diseased cells (e.g., tau, huntingtin, etc.). Alternatively, DNA for proteins not deficient or typical to the cell type, but nonetheless capable of producing some remedy could be introduced by this nanodevice. Protein sequences necessary to code for MAP-2 are well know to those skilled in the art. Reference may be had to Kindler et al., ("Molecular structure of microtubule-associated protein 2b and 2c from Rat Brain"), J. of Biological Chemistry, v265, p19679, 1990, and the like. The sequences for humans are also known. Reference may be had to the resources from the National Center for Biotechnology Information (NCBI) available online at www.ncbi.nlm.nih.gov and the human genome project.

Figure 11:
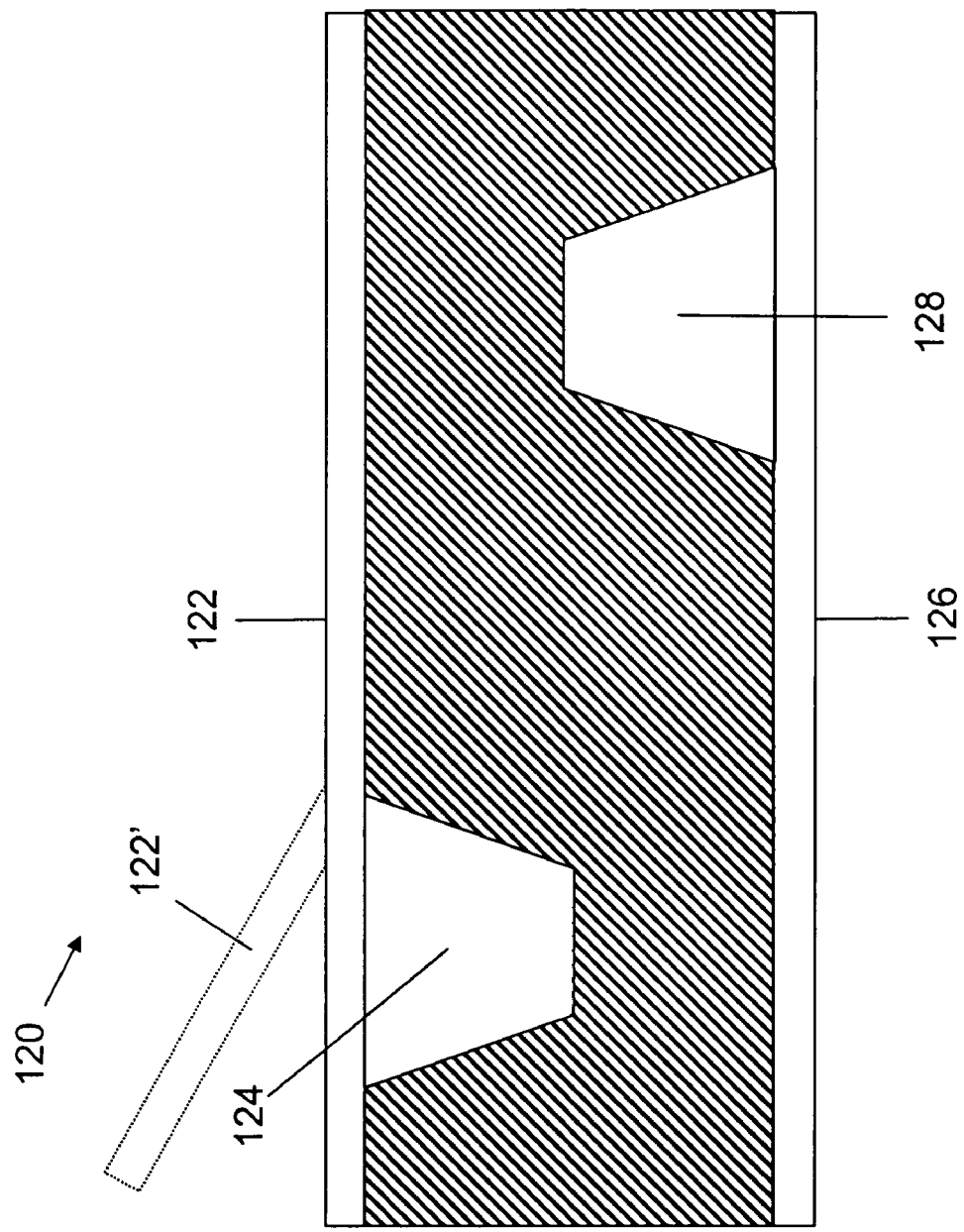
FIG. 11 is a sectional view of another embodiment of the invention, wherein multiple cavities are shown.

FIG. 11 depicts another embodiment of the invention that employs multiple cavities. In the embodiment depicted in FIG. 11, device 120 is comprised of a plurality of cavities (124, 128) and a plurality of cantilevers (122, 126). In the depicted embodiment, device 120 is rectangular. As would be apparent to those skilled in the art, the number of cavities may vary. For the sake of simplicity, only two such cavities have been illustrated. Cantilever 122' illustrates cantilever 122 in the open position.

In another embodiment, the cantilever is coated with antibodies sensitive to human cancer antigens. Reference may be had to U.S. Pat. Nos. 4,642,291; 5,134,075; 5,242,824; 6,120,767; 5,980,896; and the like, the contents of which are hereby incorporated by reference into this specification. The content of each of these patents is hereby incorporated by reference into this specification. In one such embodiment, the cantilever bends when it contacts with the aforementioned antigens and releases a therapeutic agent. In one embodiment, the aforementioned agent is a taxane. In another embodiment, it is paclitaxel.

The microparticles and microcantilevers described in this specification may be produced using techniques well known to those skilled in the art. Techniques for the production of microcapsules with controlled pore size and distribution are known. For example, one may employ traditional techniques used in microelectricalmechanical (MEM) manufacturing such as etching, masking, and the like. Reference may be had to U.S. Pat. No. 5,770,076 which is hereby incorporated by reference into this specification. Techniques for the precise control of cantilevers have found uses in atomic force microscopy (AFM). As is disclosed in the Encyclopedia of Nanoscience and Nanotechnology (volume X, pages 1–10) "single crystal and polycrystalline cantilever structures [are] routinely fabricated by a number of conventional processes of wet or dry etching. The dry etching process involves etching in an inductively coupled plasma system. Cantilevers can also be fabricated using photo-electrochemical etching using etch stops. These conventional techniques of fabricating cantilevers using micromachining techniques are ideal for cantilevers that are tens of $\mu$m in size . . . there exist a number of ways by which nanocantilevers can be fabricated such as FIB or a combination of FIB and etching." Similar techniques may be applied to the instant invention. Reference may be had to U.S. Pat. No. 6,156,216 to Manalis et al., ("Method for Making Cantilevers Devices"), U.S. patent application 2003/0045019A1 to Kubean ("Method of Fabrication of a Micro-Channel Based Integrated Sensor for Chemical and Biological Material), U.S. Pat. No. 5,581,083 to Majumdar et al., ("Method for Fabricating a Sensor on a Probe Tip Used for Atomic Force Microscopy and the Like") and the like. The content of each of the aforementioned patents and patent applications is hereby incorporated by reference into this specification.

Numerous micromachining techniques are known that produce microparticles suitable for use with the instant invention. Additionally, route micromachining may be used to join two microstructures. Reference may be had to U.S. Pat. No. 5,956,575 ("Microconnectors"), U.S. Pat. Nos. 5,976,390 ("Micromachining method and micromachined structure"), U.S. Pat. No. 6,393,685 ("Microjoinery methods and devices"), U.S. Pat. No. 5,649,423 ("Micromechanism linear actuator with capillary force sealing"), U.S. Pat. No. 5,676,850 ("Micromechanical barb and method for making the same"), U.S. Pat. No. 5,364,742 ("Micro-miniature structures and methods of fabrication thereof"), and U.S. Pat. No. 5,254,209 ("Method of making micromechanical components"). The content of each of these patents is hereby incorporated by reference.

It is, therefore, apparent that there has been provided, in accordance with the present invention, a method and apparatus for the controlled release of a compound in response to the bending of a chemically sensitive cantilever. While this invention has been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of the appended claims.

We claim:

1. A micro-device comprising a capsule comprised of a cavity, a channel connecting said cavity to an outer surface of said capsule, and a chemically sensitive cantilever, wherein said cantilever is hingably attached to said capsule, and said cantilever substantially blocks said channel, and disposed within said cavity is a taxane.

2. A micro-device as recited in claim 1 wherein said cantilever is coated with receptor particles operatively configured to bind to sensed particles, wherein the receptor particles are antibodies specific for hyperphosphorylated tau protein.

3. A micro-device as recited in claim 2 wherein said sensed particles are comprised of tau protein.

4. A micro-device as recited in claim 1 wherein said cantilever is coated with receptor particles operatively configured to bind to sensed particles and wherein the receptor particles are motor proteins.

5. A micro-device as recited in claim 4 wherein said motor proteins are comprised of kinesin.

6. A micro-device as recited in claim 5 wherein said sensed particles are microtubules.

7. A micro-device comprising a capsule comprised of a cavity, a channel connecting said cavity to an outer surface of said capsule, and a chemically sensitive cantilever, wherein said cantilever is hingably attached to said capsule, and said cantilever substantially blocks said channel, and disposed within said cavity is a taxane.

8. A process for releasing a compound comprising the steps of
    a. firstly, contacting a capsule to a first particle, wherein said capsule comprises a cavity, a compound disposed within said cavity, a channel connecting said cavity to an outer environment, a chemically sensitive cantilever substantially blocking said channel, wherein said chemically sensitive cantilever is comprised of a layer of receptor molecules which bind to said first particle,
    b. secondly, allowing said first particle to bind to said receptor molecules, thereby causing said chemically sensitive cantilever to bend, thereby substantially unblocking said channel, and
    c. thirdly, releasing said compound from said cavity to said outer environment through said channel
wherein said layer of antibodies are operatively configured to bind to hyperphosphorylated tau protein.

9. The process as recited in claim 8, wherein said compound is a taxane.

10. A micro-device comprising a capsule comprised of a cavity, a channel connecting said cavity to an outer surface of said capsule, a chemically sensitive cantilever, and a biologically active compound disposed within said cavity, wherein
    a. said cantilever is hingably attached to said capsule,
    b. said cantilever blocks said channel, and
    c. said cantilever is coated with receptor particles which are operatively configured to bind to sensed particles, thereby causing said cantilever to bend and release said biologically active compound from said cavity wherein said biologically active compound is a taxane.

11. A micro-device as recited in claim 10 wherein said receptor particles are antibodies capable of specifically binding hyperphosphorylated tau protein.

12. A micro-device as recited in claim 10 wherein said sensed particles are tau protein.

13. A micro-device as recited in claim 10 wherein said receptor particles are comprised of motor proteins.

14. A micro-device as recited in claim 13 wherein said motor proteins are comprised of kinesin.

15. A micro-device as recited in claim 14 wherein said sensed particles are microtubules.

* * * * *